US00PP16546P2

(12) United States Plant Patent
Bull

(10) Patent No.: US PP16,546 P2
(45) Date of Patent: May 16, 2006

(54) ***BIDENS* PLANT NAMED 'BIG SUNLIGHT'**

(50) Latin Name: *Bidens ferulifolia*
Varietal Denomination: Big Sunlight

(76) Inventor: Norbert Bull, Gärtnersiedlung 2, 24610 Gönnebek (DE)

( * ) Notice: Subject to any disclaimer, the term of this patent is extended or adjusted under 35 U.S.C. 154(b) by 77 days.

(21) Appl. No.: 11/022,007

(22) Filed: Dec. 24, 2004

(51) Int. Cl.
*A01H 5/00* (2006.01)

(52) U.S. Cl. ..... Plt./263
(58) Field of Classification Search ..... Plt./263
See application file for complete search history.

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Bidens* plant named 'Big Sunlight', characterized by its outwardly spreading to cascading plant habit; freely branching habit; dense and bushy appearance; large inflorescences with five to eight golden yellow-colored ray florets; and freely and continuous flowering habit.

1 Drawing Sheet

Botanical designation: *Bidens ferulifolia.*
Cultivar denomination: 'Big Sunlight'.

BACKGROUND OF THE INVENTION

The present Invention relates to a new and distinct cultivar of *Bidens* plant, botanically known as *Bidens ferulifolia* and referred to by the name 'Big Sunlight'.

The new *Bidens* is a product of a planned breeding program conducted by the Inventor in Gönnebek, Germany. The objective of the breeding program was to create new freely-branching and freely-flowering *Bidens* cultivars with attractive foliage and large flowers.

The new *Bidens* originated from a cross-pollination made by the Inventor in July, 2001 of a proprietary selection of *Bidens ferulifolia* identified as Seedling 2000-2, not patented, as the female, or seed, parent with a proprietary selection of *Bidens ferulifolia* identified as Seedling 7, not patented, as the male, or pollen, parent. The cultivar Fuego was discovered and selected by the Inventor as a flowering plant within the progeny of the stated cross-pollination in a controlled environment in Gönnebek, Germany.

Asexual propagation of the new cultivar by terminal cuttings at Gönnebek, Germany since September, 2002, has shown that the unique features of this new *Bidens* are stable and reproduced true to type in successive generations.

SUMMARY OF THE INVENTION

The cultivar 'Big Sunlight' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Big Sunlight'. These characteristics in combination distinguish 'Big Sunlight' as a new and distinct cultivar of *Bidens:*

1. Outwardly spreading to cascading plant habit.
2. Freely branching habit; dense and bushy appearance.
3. Large inflorescences with five to eight golden yellow-colored ray florets.
4. Freely and continuous flowering habit.

Compared to plants of the parent selections, plants of the new *Bidens* had larger inflorescences and more ray florets per inflorescence.

The new *Bidens* can be compared to plants of the *Bidens* cultivar Golden Star, disclosed in U.S. Plant Pat. No. 12,589. However, in side-by-side comparisons conducted in Gönnebek, Germany, plants of the new *Bidens* differed from plants of the cultivar Golden Star in the following characteristics:

1. Plants of the new *Bidens* were taller than plants of the cultivar Golden Star.
2. Leaves of plants of the new *Bidens* were shorter but broader than leaves of plants of the cultivar Golden Star.
3. Plants of the new *Bidens* had larger inflorescences and more ray and disc florets per inflorescence than plants of the cultivar Golden Star.

BRIEF DESCRIPTION OF THE PHOTOGRAPHS

The accompanying colored photographs illustrate the overall appearance of the new *Bidens*, showing the colors as true as it is reasonably possible to obtain in colored reproductions of this type. Colors in the photographs may differ slightly from the color values cited in the detailed botanical description which more accurately describe the actual colors of the new *Bidens.*

The photograph at the top of the sheet comprises a top perspective view of a typical flowering plant of 'Big Sunlight'.

The photograph at the bottom of the sheet is a close-up view of typical leaves and inflorescences of 'Big Sunlight'.

DETAILED BOTANICAL DESCRIPTION

The following observations, measurements and values describe 19-cm containers with five plants of the new cultivar grown in Gönnebek, Germany during the summer, under outdoor, full-sun conditions with day temperatures ranging from 20 to 25° C. and night temperatures ranging from 10 to 15° C. Plants used for the description were about five to six months old when the photographs and the description were taken. Color references are made to The Royal Horticultural Society Colour Chart, 1995 Edition, except where general terms of ordinary dictionary significance are used.

Botanical classification: *Bidens ferulifolia* cultivar 'Big Sunlight'.

Parentage:

*Female, or seed, parent*.—Proprietary selection of *Bidens ferulifolia* identified as Seedling 2000-2, not patented.

*Male, or pollen, parent*.—Proprietary selection of *Bidens ferulifolia* identified as Seedling 7, not patented.

Propagation:

*Type*.—By terminal cuttings.

*Time to initiate roots*.—About one week at 22° C.

*Time to develop roots*.—About two to three weeks at 22° C.

*Root description*.—Fibrous and freely branching.

Plant description:

*Appearance*.—Herbaceous container and garden plant. Outwardly spreading to cascading growth habit. Full plants with dense foliage and inflorescences held above and beyond the foliage on wiry peduncles. Moderately vigorous.

*Plant height*.—About 30 cm.

*Plant spread*.—About 35 cm.

*Lateral branches*.—Quantity: Freely branching, lateral branches potentially developing at every node. Length: About 30 cm. Diameter: About 2 mm. Internode length: About 2 cm. Texture: Smooth, glabrous. Color: Younger stems: 146D. Mature stems: Darker than 166A.

*Foliage description*.—Leaves opposite, single. Length: About 2 cm. Width: About 2 cm. Shape: Bipinnate; pinnatisect. Apex: Acute. Base: Attenuate. Texture, upper and lower surfaces: Smooth, glabrous. Petiole length: About 7 mm. Petiole diameter: About 1 mm. Petiole texture, upper and lower surfaces: Smooth, glabrous. Color: Developing foliage, upper surface: Close to 146A. Developing foliage, lower surface: 147B to 147C. Fully expanded foliage, upper surface: Between 146A and 147A; venation, similar to lamina. Fully expanded foliage, lower surface: 147B; venation, similar to lamina. Petiole, upper and lower surfaces: 147A.

Inflorescence description:

*Appearance*.—Daisy-type composite inflorescence form; actinomorphic. Disc and ray florets develop acropetally on a capitulum. Inflorescences displayed above and beyond the foliage on wiry peduncles; peduncles arising from upper leaf axils. Continuously and freely flowering; numerous inflorescences open at the same time. Inflorescences last about five days on the plant; inflorescences persistent.

*Flowering response*.—Plants flower continuously from April to October in Germany.

*Fragrance*.—Not detected.

*Inflorescence bud*.—Length: About 1.2 mm. Diameter: About 7 mm. Shape: Ovoid. Color: 12A.

*Inflorescence size*.—Diameter: About 3.5 cm. Depth (height): About 5 mm. Diameter of disc: About 7 mm.

*Ray florets*.—Length: About 2 cm. Width: About 1.1 cm. Shape: Ovate. Apex: Broadly acute or retuse. Base: Acute. Margin: Entire. Aspect: Mostly flat. Texture, upper and lower surfaces: Smooth, satiny. Number of ray florets per inflorescence: About five to eight in a single whorl. Color: When opening, upper surface: Closest to 14B. When opening, lower surface: 12A; venation, 146B. Fully opened, upper surface: 12A; color becoming closer to 12B with development. Fully opened, upper surface: 12B; venation, 146C.

*Disc florets*.—Shape: Tubular; fluted at apex. Number of disc florets per inflorescence: About 45. Length: About 8 mm. Diameter: About: 1 mm. Color: Immature: 146D. Mature: Towards the apex, 17C; towards the base, 145C.

*Peduncles*.—Length: About 1.5 to 4.5 cm. Diameter: About 1 mm. Aspect: Flexible, wiry, strong; inflorescences held above and beyond foliage. Orientation: About 30 to 45° to the stem. Texture: Smooth, glabrous. Color: 146B to 146C.

*Reproductive organs*.—Androecium: Present on disc florets only. Stamen quantity: Five per disc floret. Anther shape: Elongate. Anther color: 17A. Pollen amount: Moderate. Pollen color: 17A. Gynoecium: Present on ray and disc florets. Seed: Seed development has not been observed.

Disease/pest resistance: Resistance to pathogens and pests common to *Bidens* has not been observed on plants of the new *Bidens*.

Temperature tolerance: Plants of the new *Bidens* have been observed to tolerate temperatures from about 2 to 35° C.

It is claimed:

1. A new and distinct cultivar of *Bidens* plant named 'Big Sunlight', as illustrated and described.

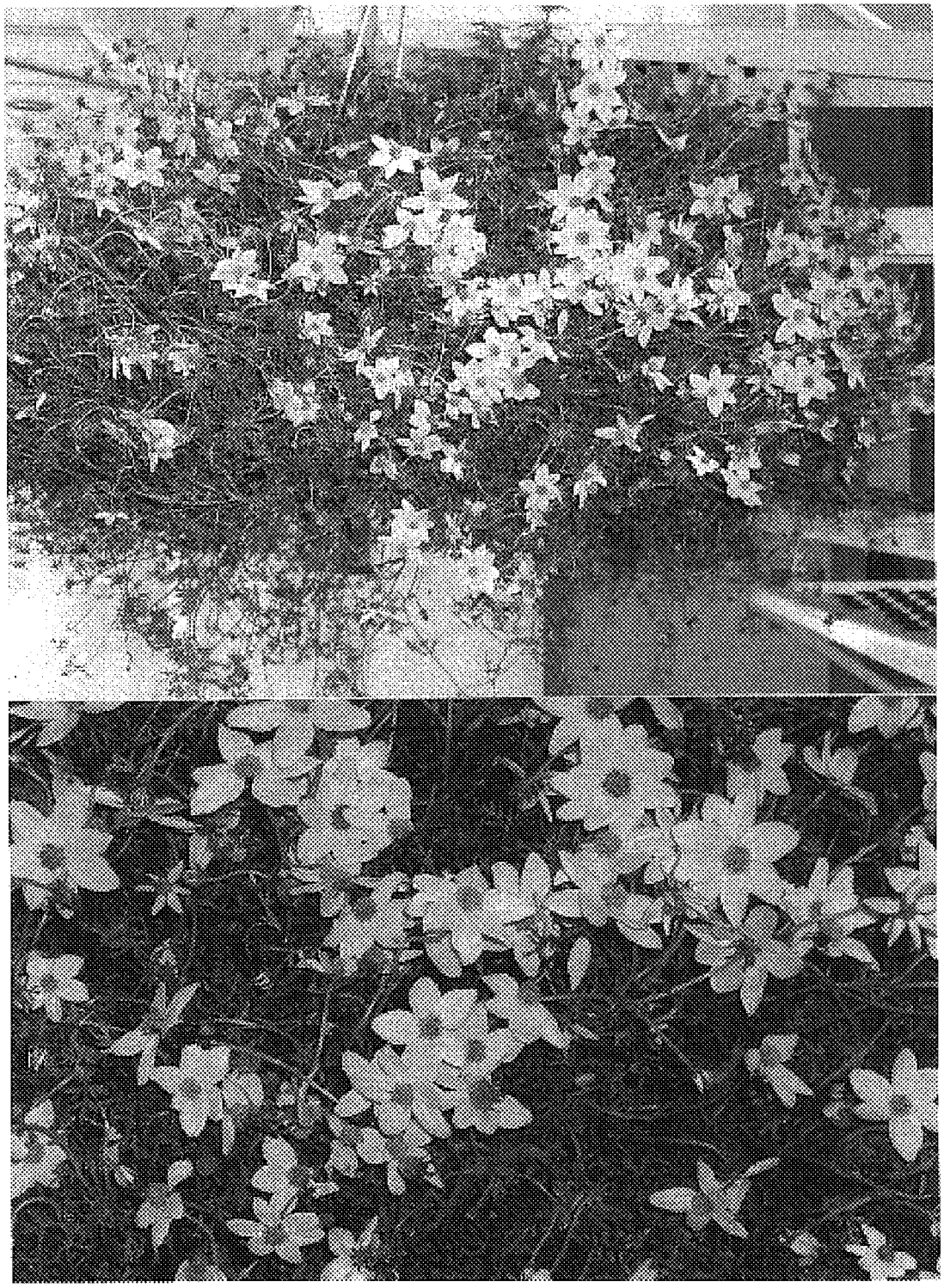

* * * * *